United States Patent [19]

Ackerman

[11] Patent Number: 5,496,290

[45] Date of Patent: Mar. 5, 1996

[54] WOUND IRRIGATION SPLASH SHIELD

[75] Inventor: Bernard Ackerman, Metuchen, N.J.

[73] Assignee: Ackrad Laboratories, Inc., Cranford, N.J.

[21] Appl. No.: 344,728

[22] Filed: Nov. 23, 1994

[51] Int. Cl.[6] .......................... A61M 37/00; A61C 1/16
[52] U.S. Cl. ........................................ 604/268; 433/116
[58] Field of Search ............................ 604/260; 433/80, 433/116; 132/322

[56] References Cited

U.S. PATENT DOCUMENTS

| 724,913 | 4/1903 | Montgomery . | |
|---|---|---|---|
| 1,216,311 | 2/1917 | Hartman | 433/116 |
| 1,934,046 | 11/1933 | Demarchi . | |
| 2,764,975 | 10/1956 | Grennberg . | |
| 2,845,064 | 7/1958 | Gabriel . | |
| 3,896,810 | 7/1975 | Akiyama . | |
| 4,424,036 | 1/1984 | Lokken | 433/116 |
| 4,692,140 | 9/1987 | Olson . | |
| 4,769,003 | 9/1988 | Stamler . | |
| 5,067,899 | 11/1991 | Paschal | 433/116 |
| 5,197,876 | 3/1993 | Coston | 433/116 |
| 5,275,559 | 1/1994 | Rihel | 433/116 |
| 5,354,267 | 10/1994 | Niermann et al. . | |
| 5,376,003 | 12/1994 | Rizkalla | 433/116 |

FOREIGN PATENT DOCUMENTS

| 14652 | 10/1933 | Australia | 433/80 |
|---|---|---|---|

OTHER PUBLICATIONS

Widgets and Gadgets in Emergency Medicine, Zerowet, Inc. –excerpt from article published in A Newsletter and Forum for the California Emergency Physician.
Photocopy–flat splash shield, Acrad Laboratories, Inc.

Primary Examiner—Paul J. Hirsch
Attorney, Agent, or Firm—Plevy & Associates

[57] ABSTRACT

A device for the prevention of contamination of medical personnel from a patient's body secretions that may splash back during wound irrigation. The splash shield has a peripheral edge that is substantially circular. The splash shield has a flat center region which forms the middle of the splash shield encircled by an outer concave region. The outer concave region curves away from the flat center region. A peripheral edge is located at the rim of the outer concave region. The peripheral edge is flat and extends outwardly from the outer concave region in a plane substantially parallel to the flat center region. A hollow conical protrusion extends through the splash shield at a point eccentric to its center. The conical protrusion has a base that lays flush against the flat center region. As the conical protrusion extends away from the flat center region, it tapers to a top surface. Moving along the conical protrusion from the base to the top surface, the cross-sectional diameter of the aperture defined by the conical protrusion decreases in length. The cross-sectional diameter of the aperture defined by the conical protrusion is dimensioned such that a friction fit is created between the interior of the conical protrusion and the flexible tip of a syringe when inserted therein.

16 Claims, 3 Drawing Sheets

WOUND IRRIGATION SPLASH SHIELD

FIELD OF THE INVENTION

The present invention relates to medical shield devices that protect medical personnel from patient body secretions that splash back during wound irrigation. More particularly, the present invention relates to transparent guards that couple directly to such wound irrigating devices.

BACKGROUND OF THE INVENTION

Irrigation of wounds is a commonly used method by medical personnel to cleanse wounds of unwanted foreign matter. Typically, the irrigation is performed using a disposable syringe and hypodermic needle. Fluid from the syringe is directed under pressure at the wound to dislodge contaminates. The cleansing action necessary to rid the wound of unwanted contaminates creates a splashback of fluids and may also form an aerosol containing both the irrigating fluid and blood droplets. This splashback is undesirable because the medical personnel carrying out the irrigation can be exposed to contaminants contained in the patient's blood.

A great concern of medical personnel is the possible transmission of infectious disease during the irrigation process. This occurs primarily through the fluids which splash back. It is impossible for medical personnel to visually determine if blood from a wound site is carrying infectious diseases such as hepatitis or HIV. Although goggles and facemasks will protect the wearer, those who are unprotected may fall victim to a disease transmitted in the splashback.

There have been many attempts in the prior art to contain the splashback, but none have proven to be completely effective.

Another possibility of transmission of infectious disease exists when the person performing the irrigation is accidentally pierced by the hypodermic needle of the syringe. Splashback may contact the hypodermic needle as the irrigation is performed. As the supply of irrigating fluid is exhausted, which takes a matter of seconds, it must be refilled. This necessitates that the syringe be refilled several times while performing a typical irrigation. Each time the syringe is filled there is a chance of an accidental contact with the hypodermic needle. Thus, the greater the number of times the syringe is refilled, the higher the probability that the person performing the irrigation will contact the hypodermic needle and possibly contact an infectious disease.

Flat, circular splash shields have been utilized in the prior art with irrigation devices for the purpose of preventing the fluids from splashing back toward the irrigating device. These types of devices are typically thin pieces of plastic through which is formed an aperture. This type of splash shield is designed to protect the person performing the irrigation from splashback, but does not adequately protect others at the surgical site from contamination. A disadvantage of this type of splash shield is inherent in the flat surface and a poor frictional gripping aperture which may cause the shield to dislodge. Should the splash shield separate from the flexible tip, the splash shield would provide no protection whatsoever to the person performing the irrigation.

U.S. Pat. No. 4,769,003, to Stamler entitled WOUND IRRIGATION SPLASHBACK SHIELD, discloses a device which attempts to contain the splashback by employing an elongated parabolic shield. The shield attaches to a syringe which is inserted into the apex of the parabolic shield. In the preferred embodiment, the shield is elongated to a length of 12 cm from the apex of the shield to its rim. The Stamler patent states the device should be used with the rim of the shield 1 cm to 3 cm from the wound. This requires the irrigation stream to travel the length of the shield and the gap between the shield and the wound in order to cleanse the wound. The disadvantage of this device is that medical personnel cannot get close to the wound to perform the irrigation or to irrigate from the inside of the wound, which is often desirable and necessary. The Stamler patent illustrates the effectiveness of the device when the irrigation takes place at a very small angle of incidence to the wound site. During an irrigation procedure, there often occurs a situation where it is desirable to deliver the irrigation fluid at a large angle of incidence to the wound site. It appears in this situation as if the irrigation fluid will splashback in a manner such that the shield will not prevent the fluids from contacting other medical personnel at the surgical site.

U.S. Pat. No. 4,692,140, to Olson entitled LAVAGE/SUCTION TIP WITH DUAL SPLASH SHIELD discloses a device which includes an elongated barrel to deliver fluid and a pair of splash shields. This device is attached to a corresponding handpiece which supplies the irrigation fluid. The first splash shield is bonded to the distal end of the barrel of the device. The second shield is slidable along the barrel to a position chosen by the person performing the irrigation. This device has the splash shields directly incorporated onto the barrel. It appears that commonly used surgical equipment to irrigate wounds, such as syringes, cannot be used in conjunction with this device. This requires those who may wish to use this device to irrigate wounds to purchase the entire device. This may increase costs to hospitals. The Olson patent states that the first splash shield is preferably sized with a diameter of 1 1/4 inches. The diameter of the first splash shield limits the usefulness of the device to small wound sites. The Olson patent did not disclose a diameter for the second splash shield, but it appears to be roughly the same size as the first splash shield. The small size of the second splash shield may not provide adequate protection against fluid splashback.

The prior art demonstrates there is a need for a splash shield which is easily attached to existing medical equipment, that effectively contains the fluids which splash back and is constructed at a relatively low cost. The present invention incorporates several features and advantages to overcome the deficiencies of the prior art.

SUMMARY OF THE INVENTION

The present invention is a device for the prevention of contamination of medical personnel from a patient's body secretions that may splash back during wound irrigation. The splash shield is substantially circular and made of a transparent, rigid material. The splash shield has a flat center region encircled by an outer concave region and a hollow conical protrusion adapted to receive the tip of a syringe.

The flat center region is substantially circular and forms the middle of the splash shield. Moving radially outward from the flat center region is a concentrically located outer concave region which encircles the flat center region. The outer concave region curves in a direction toward the patient. The conical protrusion is eccentrically located in the flat center region of the splash shield. The conical protrusion is hollow defining a circle through which the tip of a syringe may pass. The conical protrusion is dimensioned such that a friction fit is created between the interior of the conical protrusion and the end of the syringe when inserted therein.

DETAILED DESCRIPTION OF THE FIGURES

Figure 1:
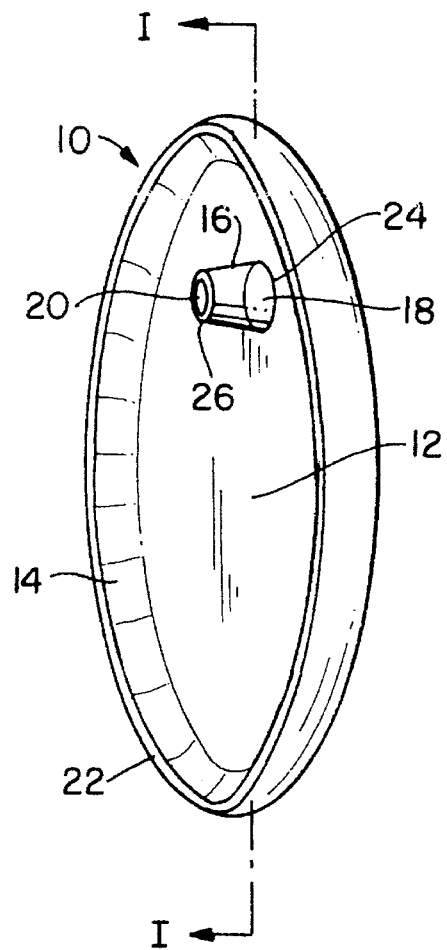
FIG. 1 is a perspective view of the first embodiment of the present invention.
Figure 2:
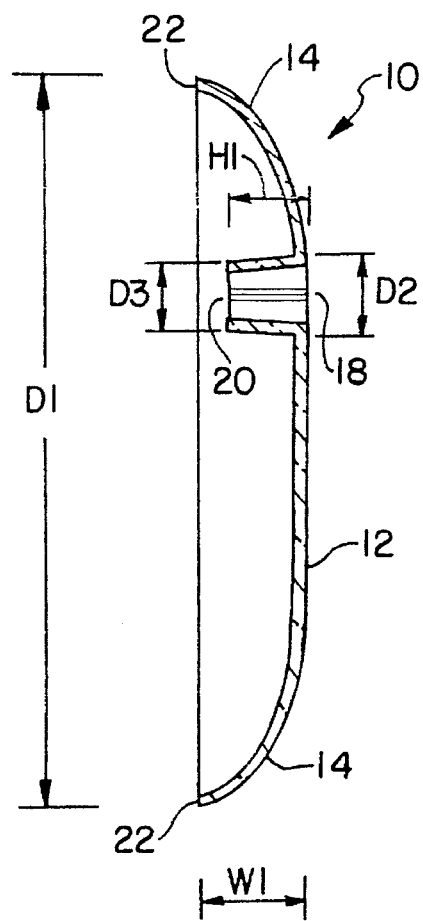
FIG. 2 is a cross-sectional view of the embodiment of FIG. 1, viewed along section line 1—1.

Referring to FIGS. 1 and 2, there is illustrated the first embodiment of the splash shield 10. The splash shield 10 has a peripheral edge 22 that is substantially circular with a diameter D1. In the preferred embodiment, the splash shield 10 is made of a transparent, rigid material, such as plastic or glass. The splash shield 10 has a flat center region 12 encircled by an outer concave region 14. A hollow conical protrusion 16 extends through the splash shield at a point eccentric to its center. The purpose of the hollow conical protrusion will later be described.

The flat center region 12 is substantially circular and forms the middle of the splash shield 10. Moving radially outward from the flat center region 12 is a concentrically located outer concave region 14 which encircles the flat center region 12. The outer concave region 14 curves away from the flat center region 12, thereby providing the splash shield 10 with an overall width W1. A peripheral edge 22 is located at the rim of the outer concave region 14. The peripheral edge 22 is flat and extends outwardly from the outer concave region 14 in a plane substantially parallel to the flat center region 12.

The conical protrusion 16 is eccentrically located in the flat center region 12 of the splash shield 10. The conical protrusion 16 has a base 24 of a first diameter D2 that lays flush against the flat center region 12. As the conical protrusion 16 extends away from the flat center region 12, it tapers down to a second diameter D3 at its top surface 26. The height H1 of the conical protrusion 16 is defined by the distance between the base 24 and the top surface 26. The height H1 of the conical protrusion 16 is preferably less than the width W1 of the splash shield 10. Moving along the conical protrusion 16 from the base to the top surface, an aperture 20 is defined by the cross-sectional diameter of the conical protrusion 16 which decreases in length.

As will be later shown, the cross-sectional diameter of the aperture 20 defined by the conical protrusion 16 is dimensioned such that a friction fit is created between the interior of the conical protrusion 16 and the end of a syringe when inserted therein.

Figure 3:
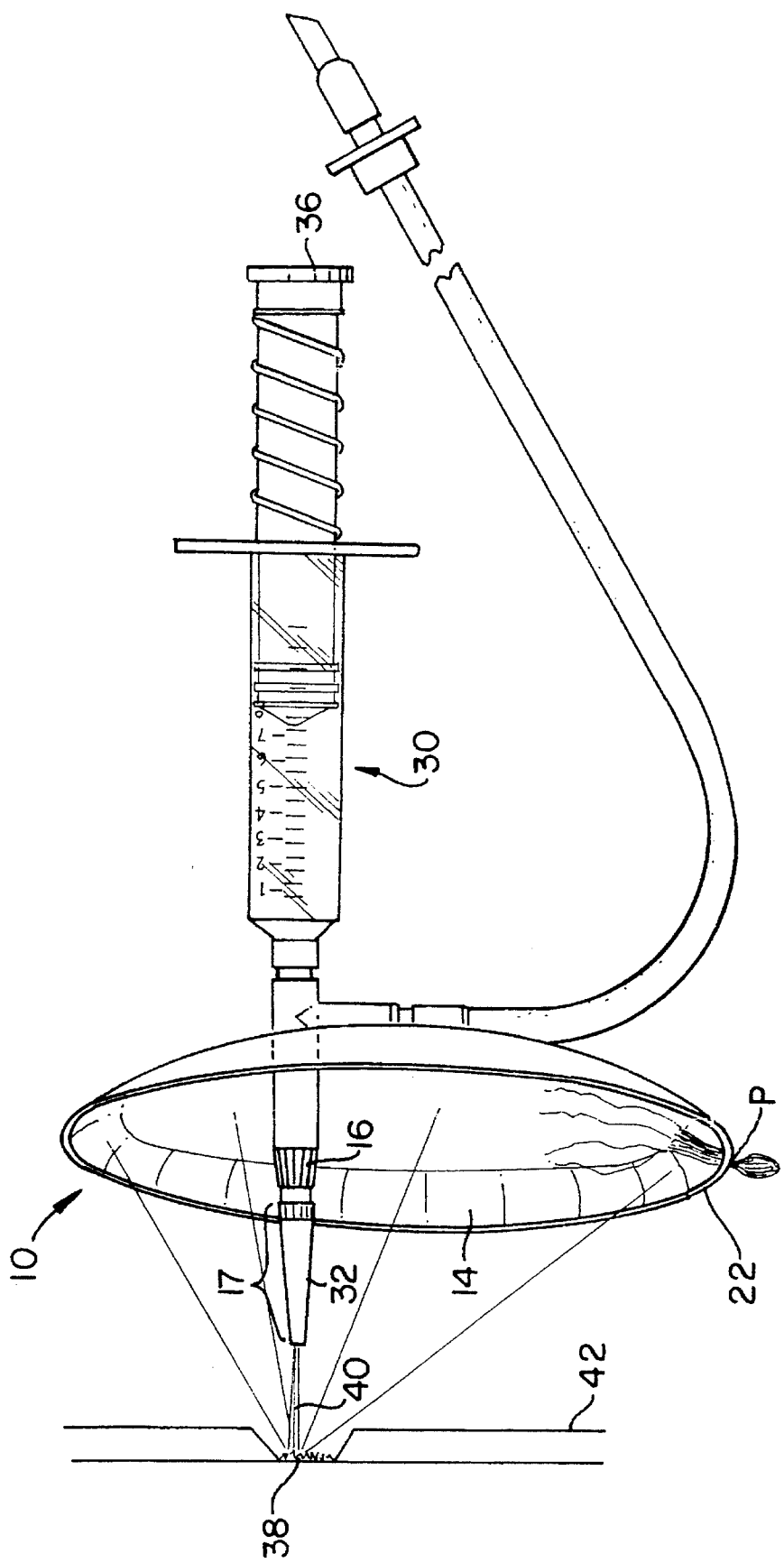
FIG. 3 is an perspective view of the first embodiment of the present invention attached to the tip or end of a syringe member.

Referring to FIG. 3, a syringe 30 is shown in conjunction with the splash shield 10. The tip or end of the syringe is coupled to a dual check valve which is known in the art and provided by the assignee herein. The distal end of the check valve incorporates a flexible tip. However, when discussing the syringe tip or end it is understood that reference is generally made to the fluid discharge outlet portion of the syringe or syringe member. It is understood that other devices or terminations can be conventionally positioned on the end of the syringe or the end or tip of the syringe may accommodate the shield directly. In this manner, the tip or end of the syringe member may be flexible or rigid. Therefore, the term syringe tip or end refers to the location which is accommodating the shield 10. The syringe 30 is coupled to a flexible irrigation tip associated with the check valve 32 that directs fluid discharged by the syringe 30. The syringe 30 is attached to the splash shield 10 by inserting the flexible tip 32 into the conical protrusion 16. A portion 17 of the tip 32 passes through the aperture 20 of the conical protrusion 16 such that the portion 17 of the flexible tip 32 extends beyond the conical protrusion 16 and the peripheral edge 22. The flexible tip 32 is tapered and creates a friction fit with the aperture 20 defined by the conical protrusion 16 as the flexible tip 32 is advanced within the conical protrusion 16. The flexible tip 32 is then placed in close proximity to or inside the wound site 38 to be irrigated. The portion 17 of the flexible tip 32 that passes through the conical protrusion 16 is the closest part of the syringe to the wound site 38. Depending upon the angle of the syringe 30 relative to the wound site 38, the splash shield 10 can be rotated about the flexible tip 32 to maximize the coverage of the wound site 38 and create the greatest level of protection from fluids splashing back.

By pressing on the plunger 36 of the syringe 30, the irrigation fluid passes through the flexible tip 32 and irrigates the wound site 38. The irregularities of the surface of the wound site 38 causes the irrigation fluid to rebound from the wound site 38 in an unpredictable direction creating potentially infectious splashback. The curvature of the outer concave region 14 of the splash shield 10 directs the accumulated splashback towards the center of the splash shield 10. The splashback runs downward and drips harmlessly from the bottom of the splash shield 10. The outer concave region 14 of the splash shield 10 acts as a catch basin that guides the splash back fluid to the bottom most point P of the splash shield 10.

The splash shield 10 is designed to be used in conjunction with a flexible tip attached to the syringe. The present invention is preferably packaged sterile and manufactured such that it is cost effective to be used once and discarded. Because the preset invention is designed to be used in conjunction with a flexible tip, the person performing the irrigation does not need to worry about accidentally contacting the sharp hypodermic needle of an ordinary syringe. The flexible tip prevents accidental exposure to disease that an ordinary hypodermic needle cannot.

Figure 4:
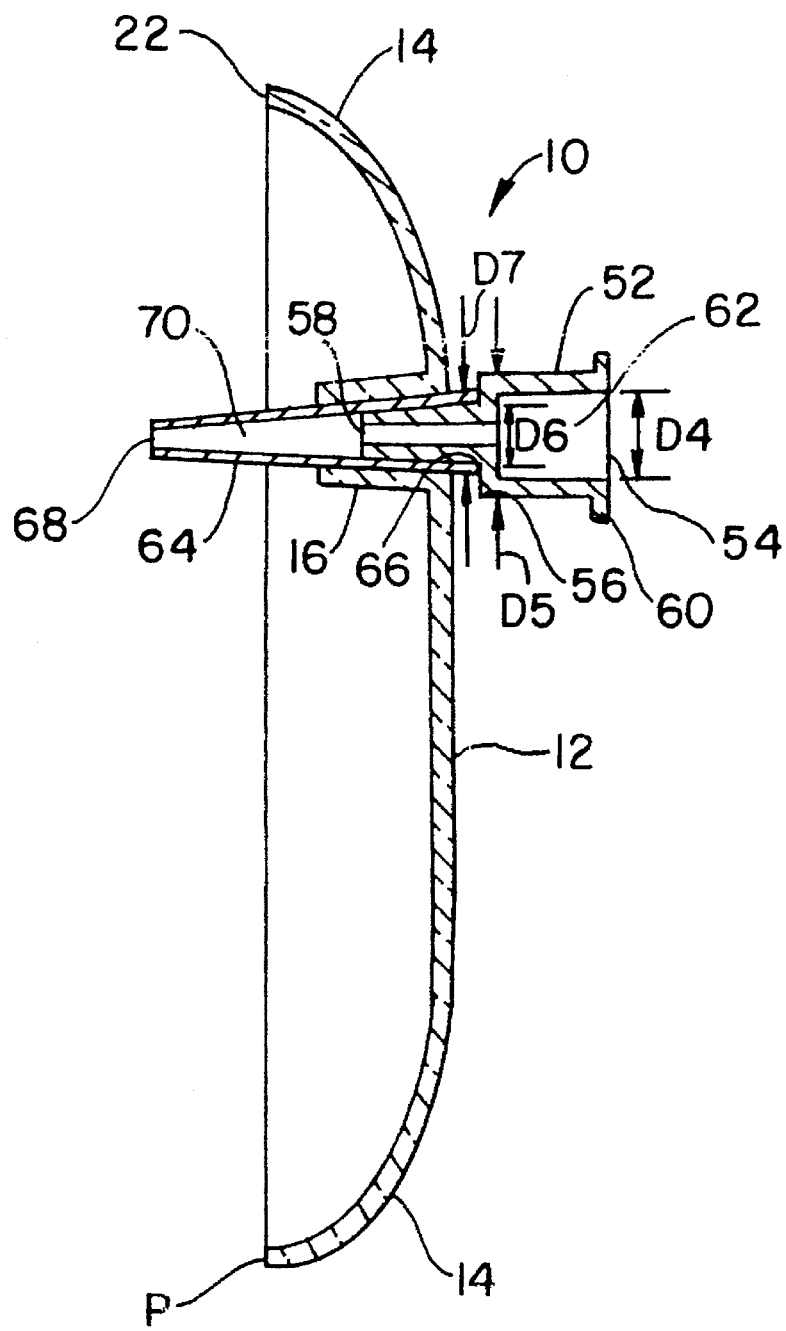
FIG. 4 is a cross-sectional view of the second embodiment as viewed along section line 1—1 of FIG. 1.

Referring to FIG. 4, there is illustrated a second embodiment of the present invention. In this embodiment, the splash shield 10 has a flat center region 12 encircled by an outer concave region 14 and a conical protrusion 16 eccentrically located about the midpoint of the splash shield 10. The flat center region 12, the outer concave region 14 and the conical protrusion 16 are similar to those in the first embodiment and are thus identified with the same reference numbers. The splash shield 10 includes a flexible tip 64 to direct the irrigation stream and a cylindrical hub 52 to attach the splash shield 10 to an irrigating device.

The cylindrical hub 52 has a base 54, a ridge 56 and a top surface 58. The base 54 has a first diameter D4 and is capable of connecting to an irrigating device. The cross-sectional diameter of the cylindrical hub 52 between the base 54 and the top surface 58 defines an aperture 62. As the cylindrical hub 52 extends away from the base 54, it tapers to a ridge 56 of a second diameter D5 located near the midpoint of the cylindrical hub 52. The portion of the aperture 62 defined by the cross-sectional diameter of the cylindrical hub 52 between the base 54 and the ridge 56 is dimensioned such that a friction fit is created between the interior of the cylindrical hub 52 and the tapered tip of a syringe when inserted therein. Extending along the cylindrical hub 52 from the ridge 56 to the top surface 58, the cylindrical hub 52 has a substantially constant cross-sectional diameter D6 which is smaller than the diameter D5 of the ridge 56. The base 54 of the cylindrical hub 52 is encircled by an annular flange 60 which extends radially outward from the outer surface of the cylindrical hub 52. The diameter of the flange 60 is sized such that the flange 60 is capable of engaging the threaded tip of a syringe.

The flexible tip 64 has a input end 66 of a diameter D7 and an output end 68. The flexible tip 64 is tapered and defines an aperture 70 which narrows moving from the input end 66 and the output end 68. The diameter of the aperture 70 is dimensioned such that a friction fit is created as the top surface 58 of the cylindrical hub 52 is inserted into the input end 66 of the flexible tip 64. The ridge 56 acts as a stop to prevent the cylindrical hub 52 from being inserted too far into the flexible tip 64. The flexible tip 64 is attached to the splash shield 10 by a friction fit with the conical protrusion 16 created as the flexible tip 64 is advanced within the conical protrusion 16. It may be desirable to adhere the flexible tip 64 to the interior surface of the conical protrusion 16 to further secure the flexible tip 64 to the splash shield 10.

To use this embodiment, a syringe with either a tapered tip or threaded tip engages the base 54 of the cylindrical hub 52. If a syringe with a tapered tip is used, the tapered tip creates a friction fit with the cylindrical hub 52 as the tapered tip is advanced within the aperture 62. Depending upon the angle of the syringe relative to the wound site, the splash shield 10 can be rotated about the tapered tip of the syringe to maximize the coverage of the wound site to be irrigated. If a syringe with a threaded tip is used, the threaded end of the syringe engage the flange 60 encircling the base 54 of the cylindrical hub 52. Depending upon the angle of the syringe relative to the wound site, the threaded-tipped syringe and the splash shield 10 must be rotated together in order to maximize the coverage of the wound site. The advantage of this embodiment is that when the splash shield is used in conjunction with a threaded-tipped syringe, there is a minimal risk of the splash shield disengaging from the syringe.

This embodiment operates similarly as the first embodiment once the splash shield 10 is connected to the syringe and the wound site is protected. The flexible tip 64 is placed in close proximity to the wound site to be irrigated. By pressing on the plunger of the syringe, the irrigation fluid passes through the flexible tip 64 and irrigates the wound site. The curvature of the outer concave region 14 of the splash shield 10 directs the accumulated splashback towards the center of the splash shield 10. The splashback runs downward and drips harmlessly from the bottom of the splash shield 10. The outer concave region 14 of the splash shield 10 acts as a catch basin the guides the splashback fluid to the bottom most point P of the splash shield 10.

It should be understood that the embodiments described herein are merely exemplary and that a person skilled in the art may make variations and modifications without departing from the spirit and scope of the invention. For example, the diameter D1 of the splash shield and the radius of curvature of the outer concave region can vary depending upon the application. The conical protrusion can define an aperture of any size depending upon the size of the flexible tip used for irrigation. Finally, the conical protrusion may be eccentrically located anywhere on the splash shield.

I claim:

1. A splash shield for use in conjunction with a fluid irrigating device having an elongated tip, said splash shield comprising:

a centrally disposed planar region having a midpoint, said centrally disposed planar region merging into an outer concave region which extends radially from said planar region, said outer concave region terminating at a rim;

connecting means located in said planar region and disposed at a point eccentric to said midpoint, for selectively connecting said splash shield to the elongated tip of the fluid irrigating device, wherein the elongated tip projects through said connecting means and extends beyond said rim.

2. The splash shield of claim 1, wherein said planar region and said outer concave region are generally circularly disposed about said midpoint.

3. The splash shield of claim 1, wherein said connecting means defines a tapered lumen through which the elongated tip of the fluid irrigating device may pass.

4. The splash shield of claim 3, wherein said tapered lumen is dimensioned to create a friction fit with the elongated tip of the fluid irrigating device when the elongated tip is inserted through said tapered lumen.

5. The splash shield of claim 1, wherein a first predetermined distance exists between the plane of said rim and said planar region, and said conical protrusion extends from said planar region by a second predetermined distance that is less than said first predetermined distance.

6. The splash shield of claim 1, wherein said planar region and said outer concave region are generally transparent.

7. A splash shield for use in conjunction with a fluid irrigating device, comprising:

a centrally disposed planar region having a midpoint, said planar region having a first surface and an opposite second surface, said centrally disposed planar region merging into an outer concave region which extends radially from said planar region, said outer concave region terminating at a rim;

a flexible tip projecting forward from said first surface to a point beyond said rim; and a cylindrical hub extending from said second surface of said planar region for receiving the fluid irrigating device and directing fluid from the fluid irrigating device into said flexible tip, wherein said cylindrical hub is disposed at a point eccentric to said midpoint.

8. The splash shield of claim 7, wherein said cylindrical hub defines a tapered lumen through which the tip of the fluid irrigating device may pass.

9. The splash shield of claim 8, wherein said tapered lumen is dimensioned to create a friction fit with the tip of the fluid irrigating device when the tip is inserted through said tapered lumen.

10. The splash shield of claim 7, wherein said cylindrical hub includes an engaging means for mechanically engaging the fluid irrigating device.

11. The splash shield of claim 10, wherein the fluid irrigating device is a syringe and said engaging means includes a thread capable of being threadedly engaged with the syringe.

12. The splash shield of claim 7, wherein said planar region and said outer concave region are generally circularly disposed about said midpoint.

13. The splash shield of claim 7, wherein said planar region and said outer concave region are generally transparent.

14. A method of irrigating a wound site to protect against fluids that splash back comprising the steps of:

providing a transparent splash shield having a centrally disposed planar region having a midpoint, said centrally disposed planar region merging into an outer concave region which extends radially from said planar region and a connecting means located eccentric to said midpoint in said planar region;

attaching an irrigating device source to said connecting means;

placing said splash shield in close proximity to said wound site;

determining the orientation of the irrigating device to properly irrigate the wound site; and positioning said splash shield in relation to said irrigating device to optimally shield the wound site; and irrigating said wound site.

15. The method of claim 14, wherein said step of positioning said splash shield further includes the step of:

rotating said splash shield relative to the irrigating device.

16. The method of claim 14, wherein said connecting means defines a tapered lumen dimensioned to create a friction fit with the fluid irrigating device when inserted therein.

* * * * *